US006652276B2

(12) United States Patent
Fischer et al.

(10) Patent No.: US 6,652,276 B2
(45) Date of Patent: Nov. 25, 2003

(54) CUSTOMIZABLE DENTAL BITE BLOCKS AND METHODS FOR FORMING CUSTOMIZED DENTAL BITE BLOCKS

(75) Inventors: Dan E. Fischer, Sandy, UT (US); Bruce S. McLean, Sandy, UT (US)

(73) Assignee: Ultradent Products, Inc., South Jordan, UT (US)

( * ) Notice: Subject to any disclaimer, the term of this patent is extended or adjusted under 35 U.S.C. 154(b) by 0 days.

(21) Appl. No.: 10/218,243

(22) Filed: Aug. 13, 2002

(65) Prior Publication Data

US 2003/0082496 A1 May 1, 2003

Related U.S. Application Data

(63) Continuation-in-part of application No. 10/002,822, filed on Nov. 1, 2001.

(51) Int. Cl.[7] .................................................. A61C 5/00
(52) U.S. Cl. ...................................... 433/140; 600/238
(58) Field of Search ............................. 433/140, 93, 94, 433/149, 136, 138; 600/237, 238, 240; 128/848, 859, 860, 861

(56) References Cited

U.S. PATENT DOCUMENTS 4,955,393 A * 9/1990 Adell .......................... 128/859
5,277,202 A * 1/1994 Hays .......................... 128/848
6,231,337 B1 * 5/2001 Boyd ............................ 433/6
2003/0003421 A1 * 1/2003 Bestenheider et al. ...... 433/215

* cited by examiner

Primary Examiner—Kevin Shaver
Assistant Examiner—Melba Bumgarner
(74) Attorney, Agent, or Firm—Workman, Nydegger & Seeley

(57) ABSTRACT

A bite block system for maintaining the mouth of the patient in an open position during a dental procedure. In one embodiment, the bite block includes a plastically deformable material on at least a surface thereof for making an impression of the patient's teeth. Such customized bite blocks provide greater safety and comfort. In another aspect, a tongue suppressing bite block system includes a bite block and a tongue suppressor adjustably attached thereto so that the tongue suppressor can be adjusted horizontally or vertically relative to the bite block to account for variations in the size of patient's mouths, teeth and tongues. In another aspect of the invention, an anatomical tongue suppressor is provided for use with a bite block. The anatomical tongue suppressor wraps around the side and underneath the tongue in order to cradle it in a more comfortable and secure fashion when in use with a bite block. The anatomical tongue suppressor may optionally include a saliva aspiration port that permits the aspiration of saliva through one or more lumens within the tongue suppressor.

57 Claims, 11 Drawing Sheets

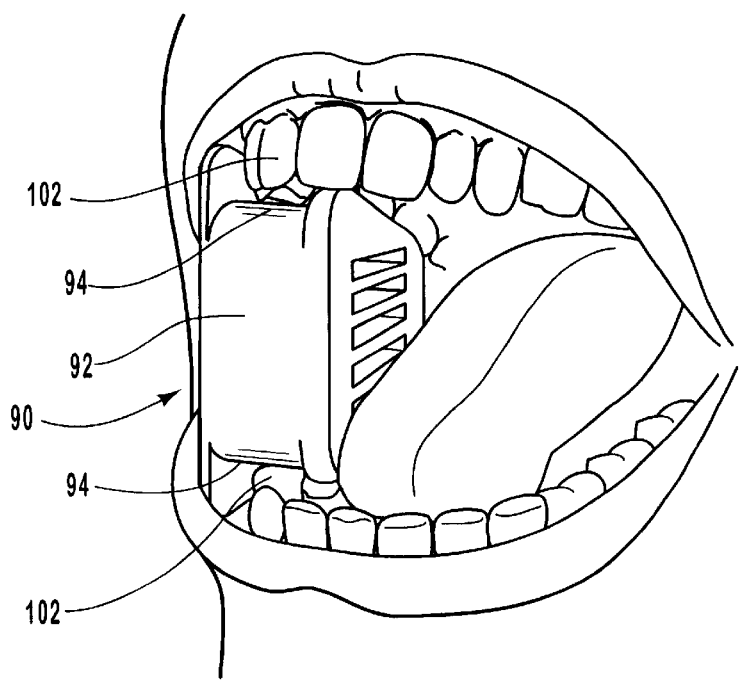
FIG. 8B
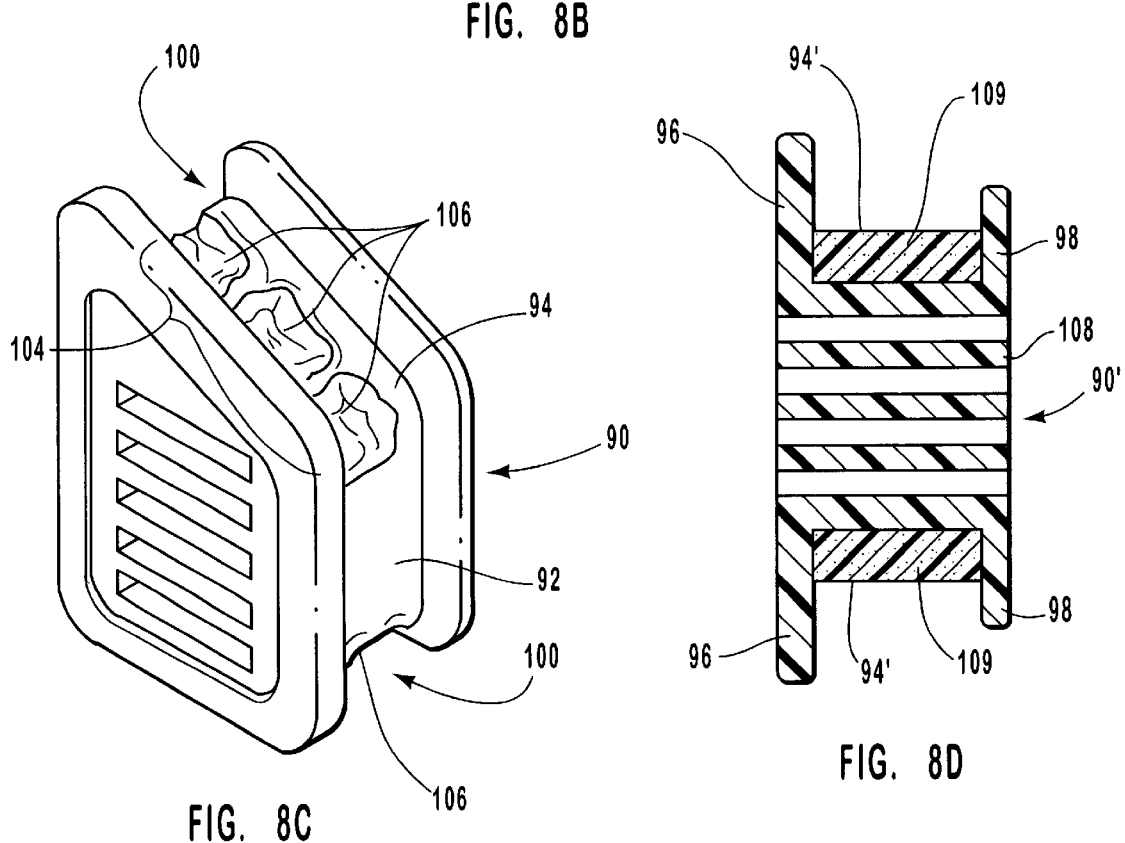
FIG. 8C
FIG. 8D

CUSTOMIZABLE DENTAL BITE BLOCKS AND METHODS FOR FORMING CUSTOMIZED DENTAL BITE BLOCKS

RELATED APPLICATION

This application is a continuation-in-part of U.S. application Ser. No. 10/002,822, filed Nov. 1, 2001. For purposes of disclosure, the foregoing application is incorporated herein.

BACKGROUND OF THE INVENTION

1. Field of the Invention

The present invention is in the field of dental bite blocks used in maintaining the mouth of a patient in an open position during a dental procedure.

2. Relevant Technology

When a dentist performs a dental procedure, it is often helpful for the patient's mouth to be held open to provide access to the patient's teeth. Some procedures, such as a simple examination or teeth cleaning, the patient may be able to open his mouth wide and long enough for the dentist or hygienist to perform the dental procedure. However, in longer and more complex procedures, the patient may tire from holding his or her mouth open or, in the alternative, be unable to hold his or her mouth open due to the pain of the dental procedure or numbness resulting from the anesthesia. In these types of procedures, dental mouth props may be used by a dentist in an effort to mechanically maintain the patient's mouth in the open position.

As appreciated by those skilled in the art, dental mouth props may function in a variety of ways. For example, some prior art dental mouth props incorporate a tubular frame inserted between the cheek and gum of a patient's mouth. Dental mouth props of this general nature generally mask the outer surface of the teeth, thereby making it difficult to view, drill, fill and/or perform other dental procedures on the teeth. Moreover, the dental mouth prop is usually positioned on both sides of the mouth, thus having the effect of obscuring the dentist's view and access from all angles within the patient's mouth.

Other dental mouth props have been developed by those skilled in the art which engage the teeth of a patient. These prior art dental mouth props are typically inserted between the upper and lower molars on one side of the mouth allowing a dentist to view and have working access to a larger area of the patient's mouth. However, these devices have no provisions for patient comfort and may cut or irritate the patient's mouth, gums and cheeks. Often these types of dental mouth prop devices are small and could be accidentally swallowed by a patient causing severe injury to the patient.

As appreciated by those skilled in the art, a patient's tongue may also interfere with a dental procedure by interfering with the dentist's visibility and by interrupting the limited available work space within the patient's mouth. Traditionally, dentists have used a variety of implements in an effort to suppress the tongue during a dental procedure. For example, dentists have used hand-held suppressors to hold the tongue in place. However, the use of hand-held tongue suppressors restricts the dentist to the use of only one hand or requires a dental assistant to hold the suppressor in place. Hand-held suppressors can therefore crowd the available working space within the mouth and prevent a clear view of the targeted work area.

In view of the foregoing, efforts have been made to integrate into a single device the ability to prop open the patient's mouth while suppressing the tongue. An example is U.S. Pat. No. 6,244,866 to Campbell, which issued Jun. 12, 2001, the disclosure of which is incorporated herein. The Campbell device includes a bite block sized and configured to engage the patient's teeth in order to thereby maintain the mouth in the desired propped-open orientation and a tongue suppressor that extends laterally from the side of the bite block. The tongue suppressor is sized and configured so as to be slidably disposed within a corresponding slot within the bite block so as to provide lateral adjustment of the tongue suppressor relative to the bite block.

Whereas the Campbell device represents an improvement over previous dental mouth props and tongue suppressors, it is limited in the range of adjustability of the tongue suppressor relative to the bite block. In view of the tremendous variability in the size and shape of the patient's mouths, dental arches, teeth and tongues, the adjustability feature provided by the Campbell device may not adequately cover all such variations in an optimal manner.

Moreover, the Campbell device is of the "one-size-fits-all" variety that is not customizable to account for variations in the size and shape of individual patient dentition. It also does not always reliably or comfortably remain in place or suppress the patient's tongue during dental procedures.

Accordingly, there exists a need for a bite block/tongue suppressor having greater adjustability so as to accommodate any and all differences in the sizes and shapes of one or more of a patients' mouths, dental arches, teeth and tongues and/or to more reliably or comfortably suppress the patient's tongue during the dental procedure.

SUMMARY OF THE INVENTION

In one aspect, the invention comprises a customizable dental bite block that can be customized to include an impression of a patient's teeth for use in maintaining the mouth of a patient in an open position. The customized bite block results in greater patient comfort, and it assists in keeping the bite block from slipping out of the patient's mouth during use. In another aspect, the invention comprises anatomical tongue suppressors, and bite blocks incorporating such tongue suppressors, that more reliably or comfortably suppress the patient's tongue. In another aspect, a tongue-suppressing bite block is provided that includes an adjustable tongue suppressor adjustably connected to the bite block.

In one embodiment of the invention, the bite block includes one or more slots configured to receive therein a corresponding portion of the tongue suppressor in an adjustable fashion. The one or more slots provide or allow for at least two modes of adjustment of the tongue suppressor relative to the bite block. The first mode of adjustment allows for lateral movement of the tongue suppressor relative to the bite block, thereby providing the ability to extend or retract the tongue suppressor in order to effectively adjust the length thereof. In this way, the position of the tongue suppressor can be adjusted in order to account for varying tongue widths among different people. This adjustment is particularly advantageous for those embodiments in which the tongue suppressor includes a flange feature that engages a side of the tongue distal to the bite block, and particularly those that wrap around and also engage a portion of the underside of the tongue.

The second mode of adjustment allows for vertical movement of the tongue suppressor relative to the bite block, thereby providing the ability to raise or lower the tongue suppressor relative to the bite block and the patient's teeth.

In this way, the position of the tongue suppressor can be adjusted upwardly or downwardly in order to account for varying tongue thicknesses among different people, tooth heights, or other variations that result in variability between the relative heights of the tongue and tooth surfaces within different people.

Other, optional modes of adjustment are also within the scope of the invention, including but not limited to, adjustments that allow for one or more angular movements of the tongue suppressor relative to the bite block (e.g., lateral, axial or both).

The bite block and tongue suppressor can be of any desired design and material. In general, the tongue suppressor includes a retention arm that extends from its engagement with the bite block across the top of the tongue. The retention arm is the primary feature of the tongue suppressor that holds the tongue and prevents it from obstructing access to the patient's teeth. The tongue suppressor may optionally include a flange or other projection at an end distal to the bite block that projects or curves downward into the inferior aspect of the oral cavity (e.g., the bottom cavity of the mouth). This flange or other projection can engage a side of the tongue opposite to the bite block in order to provide an additional tongue suppression feature in addition to the retention arm.

The retention arm may be configured to slide freely into and out of the slot. Alternatively, retention mechanisms such as a friction fit, a mechanical lock, notches and the like may be incorporated into the design of the bite block and/or the tongue suppressor to more securely hold the tongue suppressor in the slot of the bite block in a desired position.

In a more preferred embodiment, the tongue depressor includes a flange that is configured so as to curve around and under the tongue when in use in order to anatomically cradle or retain the tongue in a more secure and more comfortable fashion. This embodiment better inhibits a struggling patient from slipping his or her tongue around the side of the flange and out from under the tongue suppressor, which can potentially obstruct or inhibit the dental procedure. Thus, an anatomically shaped tongue suppressor may be used to more securely cradle and retain the tongue in a desired orientation during the dental procedure.

The bite block may be configured with one or more shoulders that extend along the sides of the teeth. These shoulders serve to position the bite block on and around the teeth and to prevent lateral slippage. Shoulders may be present on both sides of the bite block around the inside and outside of the teeth. The shoulders may be of varying heights. A lower profile interior shoulder may be less likely to rub on the roof of the mouth and cause pain or discomfort to the patient. Of course, the interior and exterior shoulders may be sized and configured in any desired fashion.

Since the bite block will generally be held in place by the teeth of a patient, it advantageously includes opposite-facing surfaces that engage the upper and lower teeth, respectively. The surfaces may be elastically (i.e., resiliently) distortable, thus allowing the teeth of the patient to slightly penetrate and temporarily deform the surface area. In this way, the surfaces can provide gentle engagement of the teeth. The surfaces may include ridges, indentations, ribs, or other features that provide mechanical means for engaging the teeth and preventing slippage of the bite block relative to the teeth.

In a more preferred embodiment, the tooth engagement surfaces and at least the immediately surrounding area may advantageously comprise a plastically deformable material that is able to at least partially received and retain an impression of the patient's teeth. For example, the engagement surface may comprise a material (e.g., a thermoplastic polymer) that, when heated, temporarily becomes plastically deformable and that, when cooled, maintains an impression of the patient's teeth absent the application of an external force. In this way, the bite block can be custom-fitted to a particular patient in order to increase patient comfort and also to more reliably maintain the bite block in the desired position and keep it from inadvertently slipping out from between the patient's teeth. The engagement surface may alternatively comprise a material (e.g., wax) that is plastically deformable at body temperature and that will at least partially retain an impression of the patient's teeth over time absent application of an impression deforming force.

The bite block may advantageously be employed on either side of the mouth, e.g., by reversing its orientation relative to the person's teeth and/or by removing and reversing the tongue suppressor relative to the bite block. The bite block may be manufactured to include an angle that matches the desired angle of an open mouth. The angle of engagement may vary depending on the age and size of a patient as well as the size of the area needed for conducting the dental procedure. The dentist may be provided with varying sized bite blocks and/or tongue suppressors to account for varying mouth sizes and shapes.

The bite block and/or tongue suppressor may be formed, if desired, with rounded edges and surfaces to prevent injury to the soft tissue. The exterior surface of the bite block may be curved, for example, to conform to the general shape of a patient's mouth. The bite blocks and/or tongue suppressor may be formed from one or more materials selected for their low cost and/or disposability. In addition, they may be pre-sterilized and packaged. Moreover, they may be treated with a desired flavoring.

These and other features of the present invention will become more fully apparent from the following description and appended claims, or may be learned by the practice of the invention as set forth hereinafter.

BRIEF DESCRIPTION OF THE DRAWINGS

In order that the manner in which the above-recited and other advantages and objects of the invention are obtained, a more particular description of the invention briefly described above will be rendered by reference to a specific embodiment thereof which is illustrated in the appended drawings. Understanding that these drawings depict only a typical embodiment of the invention and are not therefore to be considered to be limiting of its scope, the invention will be described and explained with additional specificity and detail through the use of the accompanying drawings, in which:

FIGS. 8A–8D depict a customizable bite block according to the invention that is able to receive and retain an impression of a patient's teeth;

DETAILED DESCRIPTION OF THE PREFERRED EMBODIMENTS

In order to better illustrate the structural and functional features of the various embodiments of inventive bite blocks according to the invention, the following detailed description is presented. It should be understood that the components of the present invention, as generally described and illustrated in the figures herein, could be arranged and designed in a wide variety of different configurations. Thus, the following detailed description of the invention, and as illustrated in FIGS. 1–15, is not intended to limit the scope of the invention, but is merely representative of the presently preferred embodiments of the invention.

As will be shown hereafter, one aspect of the invention involves the ability to adjust a tongue suppressor relative to a bite block. In another aspect of the invention, a bite block is provided that is customizable so as to make and maintain an impression of a particular patient's teeth. In yet another aspect of the invention, a tongue-suppressing bite block system includes a tongue suppressor that is anatomically configured so as to wrap around and cradle the patient's tongue in order to better restrain movement of the tongue during a dental procedure.

Figure 1:
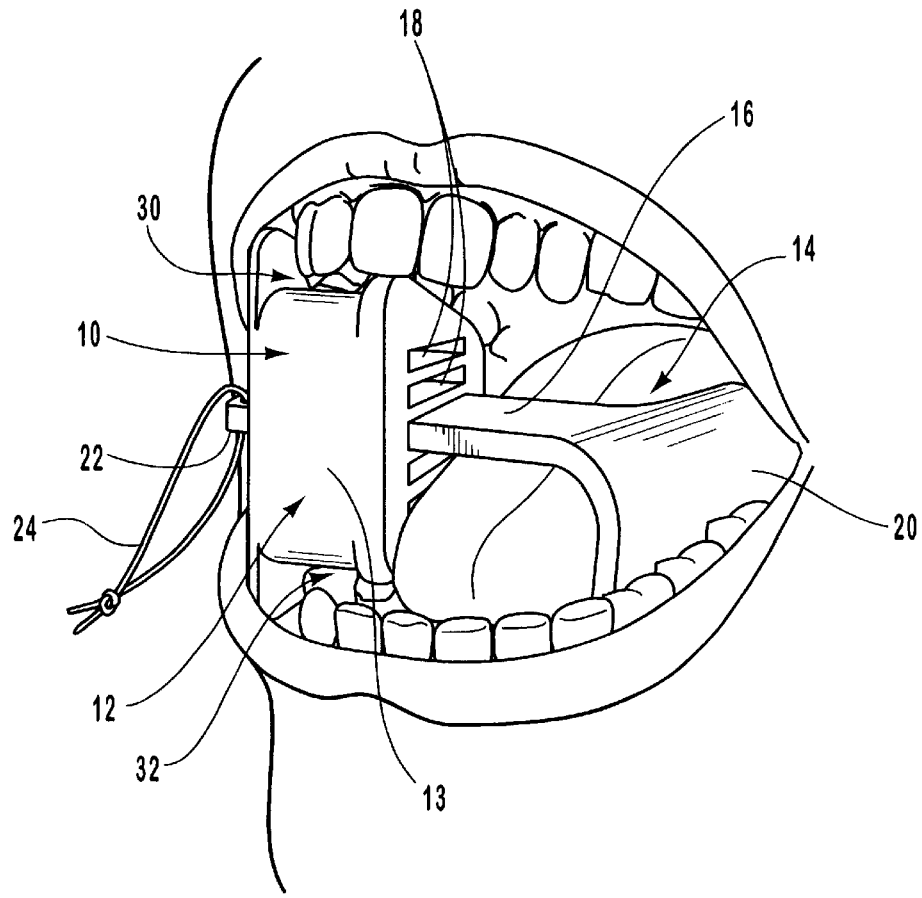
FIG. 1 is a perspective view of an embodiment of an adjustable tongue suppressing bite block that includes multiple slots in the bite block for vertical adjustment of the tongue suppressor and that is shown inserted within a patient's mouth.
Figure 2:
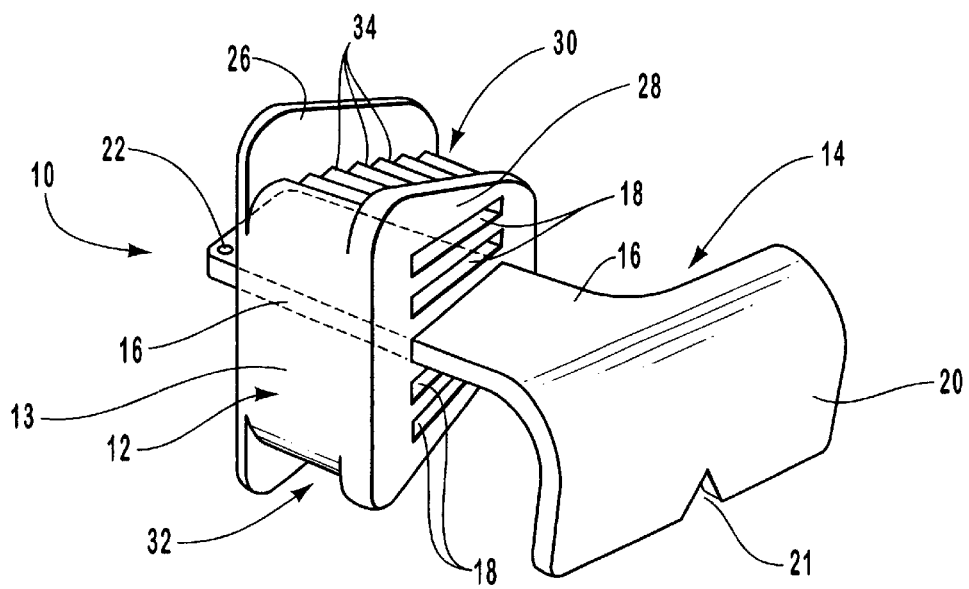
FIG. 2 is a perspective view of the embodiment illustrated in FIG. 1.
Figure 3:
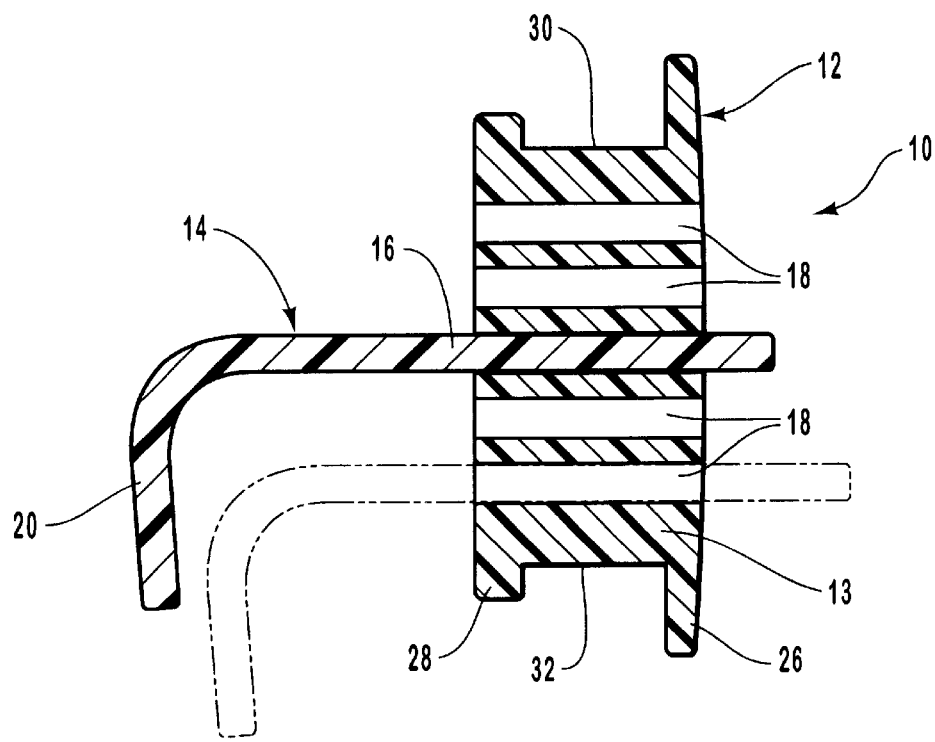
FIG. 3 is a cross-sectional view of the embodiment illustrated in FIGS. 1 and 2 depicting the vertical adjustability of the tongue suppressor relative to the bite block.

Reference is now made to FIGS. 1–3, which depict an embodiment of the invention that includes features for both lateral and vertical adjustability of the tongue suppression element. More particularly, these figures depict a tongue suppressing bite block system 10 that includes a bite block 12 and a tongue suppressor 14 connected or attached to a body 13 of the bite block 12 in an adjustable fashion, and adjustment means for selective lateral and vertical movement of a tongue suppressor relative to the bite block 12. The bite block 12 is sized and configured for positioning in a person's mouth in order to maintain the person's mouth in an open position, while the tongue suppressor is oriented relative to the bite block so as to maintain the person's tongue within a confined region of the person's oral cavity when the bite block is positioned within the person's mouth.

The tongue suppressor 14 includes a retention arm 16 that is sized and configured so as to be slidably inserted into or retracted from within any one of a plurality of adjustment slots 18 within the bite block body 13. This ability of the retention arm 16 to be selectively inserted or withdrawn from slots 18 provides two degrees of adjustability. First, selective insertion or retraction of the retention arm 16 relative to a single adjustment slot 18 results in the ability to lengthen or shorten the tongue suppressor 14 relative to the bite block 12. In this way, the tongue suppressing bite block 10 can account for, and be adjusted to accommodate, varying widths of tongues among different patients.

In addition, by withdrawing the retention arm 16 entirely from one adjustment slot 18 and then inserting it into another slot 18, the position of the tongue suppressor can be adjusted vertically relative to the bite block 12. In this way, the tongue suppressing bite block 10 can accommodate the great variability that exists between differently sized teeth, tongues, mouths, and the like among different patients. This function is a great improvement in the art, and it goes far beyond simply providing for lateral adjustability, as is the case where the bite block only includes a single slot for receipt of the retention arm.

The embodiment depicted in FIGS. 1–3 includes five adjustment slots 18. It will be appreciated, however, that any number of adjustment slots 18 may be included within the bite block body 13 in order to provide the desired level of vertical adjustability. The only limitation to the number of slots is the size of the bite block body 13 and the depth of the slots 18 and retention arm 16. Moreover, even though the adjustment slots 18 are depicted as being substantially parallel, it will be appreciated that the slots 18 can be angularly off-set one from another in order to provide different angular orientations, or pitches, of the tongue suppressor 14 relative to the bite block 12, thus providing greater adjustability and variability of the tongue suppressor 14 relative to the bite block 12. Accordingly, the interaction between the retention arm 16 and adjustment slots 18 comprise an example of the aforementioned adjustment means, as do any of the suggested variations.

The retention arm 16 of the tongue suppressor 14 may be sized and configured relative to the adjustment slots 18 so as to result in sufficient friction such that positive force is required to either advance or retract the retention arm 16 relative to the slots 18 of the bite block body 13. In this way, the tongue suppressor 14 will tend to remain in a desired lateral orientation relative to the bite bock 12.

The tongue suppressor 14 further includes a flange or protruding portion 20 that curves or otherwise angles around the side of the patient's tongue in order to maintain the tongue at a desired spaced-apart relationship relative to the adjacent teeth (i.e., those teeth opposite the bite block 12). The interface between the flange 20 and the retention arm 16 is preferably curved for comfort and to better conform to the generally curved shape of the side of the tongue. The flange 20 ensures less obstructed access by the dentist or practitioner to the patient's teeth adjacent to the flange 20. In general, the retention arm 16 and flange 20 work together to maintain the tongue in a desired suppressed orientation within the mouth in a comfortable manner. Nevertheless, it will be appreciated that the tongue suppressor 14 need not include the flange 20 but may merely comprise the retention arm 16 in order to generally suppress the tongue at the bottom of the oral cavity. In another embodiment discussed below (FIGS. 11–13), an anatomical tongue suppressor curves around the side and under the tongue so as to cradle it.

As depicted in FIGS. 1–3, the flange 20 may extend rearwardly beyond the width of the retention arm 16 in order to provide tongue suppression further back within the patient's mouth so as to maintain the tongue away from the patient's molars. Although the retention arm 16 is depicted as having a single width so as to be fully insertable into one of the adjustment slots 18, it will be appreciated that the retention arm 16 may have varying widths with one width, for example, sized so as to fit within one of the adjustment slots 18, and another width (not shown) sized so as to provide a desired tongue suppression function independent of the function of insertion or retraction of the retention arm 16 into the slots 18 of the bite block body 13.

In order to further assist the dentist or other practitioner in carrying out a desired dental procedure, the flange 20 may include an aspiration notch 21 in order to facilitate aspiration and removal of excess saliva, other liquids or debris from within the oral cavity, which tend to build up when the patient's mouth is open and the patient is unable to swallow or expel fluid from the oral cavity.

In order to provide additional safety, the tongue suppressing bite block 10 system may include means for attaching a leash or other safety feature when retrieval of the bite block from deep within the patient's mouth becomes necessary. For example, a leash hole 22 may be provided within the retention arm 16 for attachment of a leash 24 thereto.

As illustrated in FIGS. 1–3, the bite block body 13 is advantageously tapered from front to back in order to match the angle of an opened mouth. It will be appreciated that the angle of the bite block body 13 may be varied from one device to another depending on the size of the patient's mouth and the degree of opening or closure that is desired. For example, if the dentist desires a larger work area or access to the teeth in the rear of the patient's mouth, the angle of the bite block body 13 may be steeper in order to force the patient's mouth in a more open configuration. Conversely, the angle of the bite block body 13 may be less, and the bite block body 13 narrower, in the event that it is desired to work on the front teeth and where greater patient comfort is desired.

In order to maintain the bite block 12 in a desired position relative to one side of the patient's teeth, the bite block 12 may include an outer shoulder 26 and an inner shoulder 28 that extend from beyond an upper surface 30 and a lower surface 32 of the bite block body 13 in order to effectively form a channel into which the teeth may be inserted during use. In this way, the outer shoulder 26 and inner shoulder 28 serve to prevent lateral movement of the bite block 12 relative to the patient's teeth in addition to whatever retention forces may be provided by the patient when simply biting down onto the bite block 12 in manner so that the patient's upper teeth engage the upper surface 30 and the lower teeth engage the lower surface 32 of the bite block body 13.

The outer and inner shoulders 26, 28 may be formed having different heights. For example, the height of the outer shoulder 26 may be greater than the height of the inner shoulder 28 in order to provide greater retention while maintaining patient comfort in view of the anatomy of the oral cavity surrounding the teeth.

In order to provide additional retention, the upper and lower surfaces 30, 32 may include ridges 34 that provide additional gripping ability or mechanical interaction between the patient's teeth and the upper and lower surfaces 30, 32 of the bite block 12. In other embodiments discussed below (FIGS. 8–10), the upper and lower surfaces of the bite block body may comprise an impression material that is plastically deformable at a predetermined temperature or temperature range. In this way a custom-fitted bite block containing an impression of a patient's teeth can be manufactured.

Figure 4:
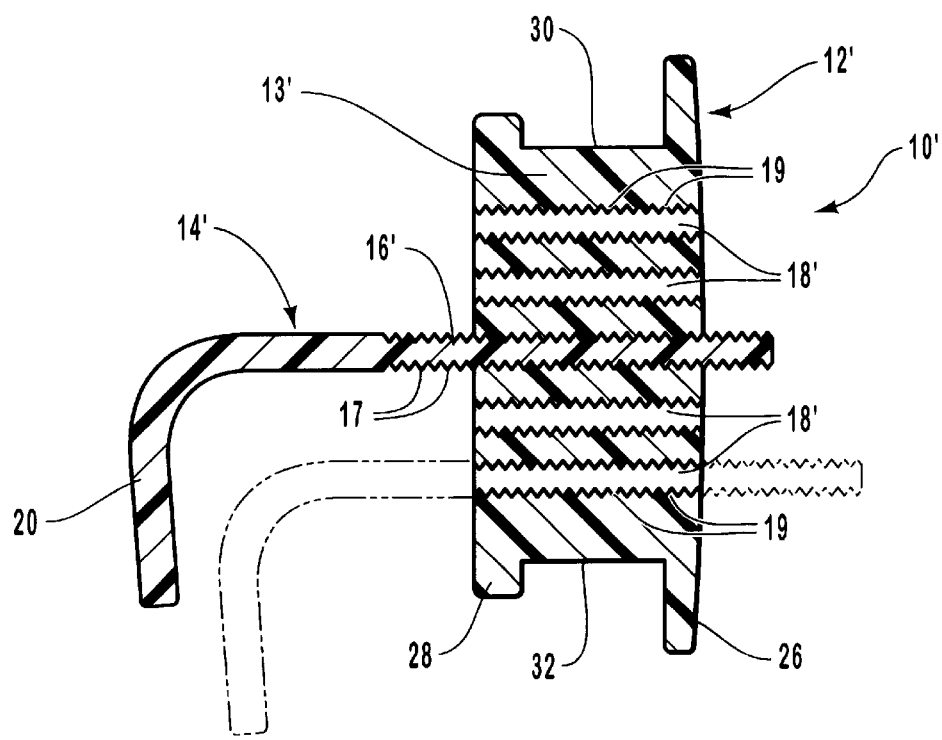
FIG. 4 is a cross-sectional view of an alternative embodiment of an adjustable tongue suppressing bite block that includes locking notches designed to partially restrict lateral movement of the tongue suppressor relative to the bite block.

FIG. 4 depicts an alternative embodiment of a tongue suppressing bite block system 10' that includes features for temporarily locking a tongue suppressor 14' within one of a plurality of adjustment slots 18' within a body 13' of a bite block 12'. In particular, the retention arm 16' of the tongue suppressor 14' includes a plurality of retention arm locking notches 17 that are sized and configured so as to engage corresponding slot locking notches 19 formed within the adjustment slots 18' of the bite block body 13'. In this way, a force great enough to dislodge the arm locking notches 17 from within the slot locking notches 19 must generally be applied to insert or retract the retention arm 16' relative to one of the adjustment slots 18'. In most other respects, the tongue suppressing bite block system 10' of FIG. 4 is substantially similar to the tongue suppressing bite block system 10 depicted in FIGS. 1–3. The retention arm 16', adjustment slots 18', arm locking notches 17 and slot locking notches 19 comprise adjustment means according to the invention.

Figure 5:
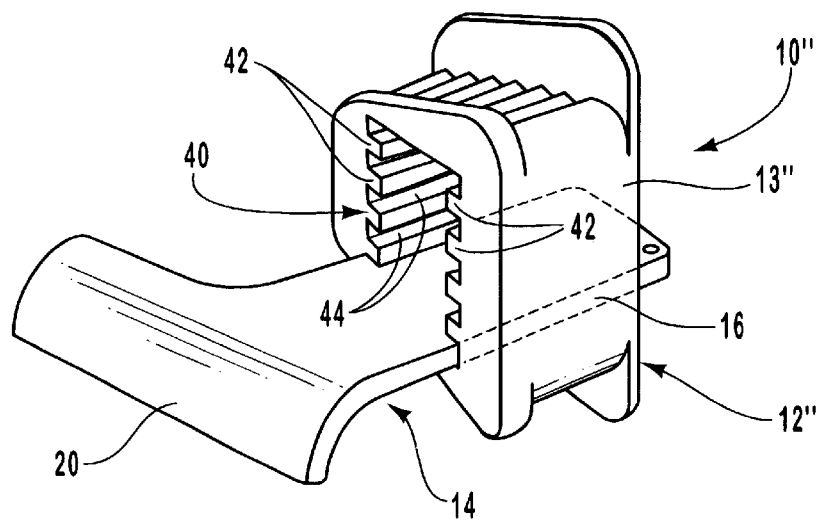
FIG. 5 is a perspective view of an alternative embodiment of a tongue suppressing bite block that includes a single opening and multiple ridges therein that provide both lateral and vertical adjustability of the tongue suppressor.

FIG. 5 depicts another embodiment of a tongue suppressing bite block system 10" that includes a bite block 12" having a body 13" and a tongue suppressor 14 that is substantially identical to the tongue suppressor 14 that is depicted in FIGS. 1–3. Instead of the plurality of adjustment slots 18 depicted in FIGS. 1–3, the bite block body 13" in the embodiment of FIG. 5 includes a cavity 40 having a plurality of adjustment ridges 42 that define a plurality of adjustment recesses 44 into which the retention arm 16 may be selectively inserted. The adjustment ridges 42 and recesses 44 are sized and configured so as to define what are essentially a plurality of adjustment slots that are akin to the adjustment slots 18 depicted in FIGS. 1–3. The retention arm 16, cavity 40, adjustment ridges 42, and adjustment recesses 44 comprise adjustment means for selective vertical and lateral movement of a tongue suppressor relative to a bite block.

The main difference between the embodiment depicted in FIG. 5 is that it requires less material to manufacture than the embodiment depicted in FIGS. 1–3, thereby decreasing the materials cost of the bite block 12" of the embodiment in FIG. 5 relative to the bite block 12 depicted in FIGS. 1–3. In most other respects, the tongue suppressing bite block system 10" of FIG. 5 functions in substantially the same manner as the embodiment of FIGS. 1–3.

Figure 6:
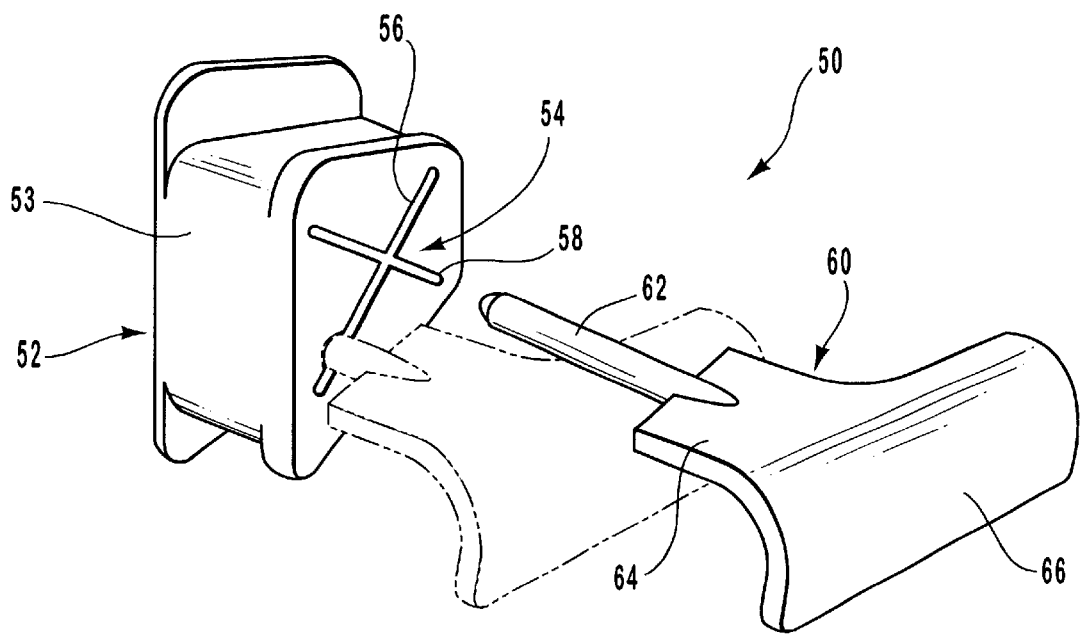
FIG. 6 is a perspective view of an alternative embodiment of a tongue suppressing bite block in which the tongue suppressor is adjustable upwardly, downwardly, forwardly, and backwardly relative to the bite block.

FIG. 6 depicts yet another embodiment of a tongue suppressing bite block system 50 according to the invention configured for even greater adjustability. More particularly, the tongue suppressing bite block system 50 comprises a bite block 52 having a body 53 that includes a criss-crossing slot system 54 that provides greater degrees of adjustability of the tongue suppressing means relative to other embodiments. The slot system 54 includes a first compression slot 56 extending from the front lower end of the bite block body 53 and extending to the rear upper end and a second compression slot 58 extending from the front upper end to the rear lower end of the bite block body 53.

A tongue suppressor 60 is provided that includes an insertion peg 62 sized and configured so as to be inserted into one of the compression slots 56, 58 of the slot system 54. The insertion peg 62 is advantageously of greater diameter than the widths of the first and second compression slots 56, 58, and the bite block body 53 advantageously comprises a resilient and flexible material, at least in the region of the slot system 54, in order for the compression slots 56, 58 to flex open so as to receive therein the insertion peg 62. The resiliency of the bite block body 53 in the region of the slot system 54 causes the compression slots 56, 58 to exert sufficient gripping and/or frictional forces onto the insertion peg 62 so as to retain the tongue suppressor 60 in a desired vertical, angular, horizontal, and lateral orientation relative to the bite block 52. The bite block body 53 is sufficiently flexible, however, in the region of the slot system 54 so as to allow for movement of the insertion peg 62 within the slot system 54 by exerting enough force on to the tongue suppressor 60 to overcome the retention forces exerted onto the insertion peg 62 by one or more compression slots 56, 58. This allows adjustment of the position of the tongue suppressor 60 relative to the bite block 52 so as to assume one of a large variety of varying vertical, horizontal, angular and lateral orientations relative to the bite block 52. The slot system 54 and insertion peg 62 comprise adjustment means for selective lateral and vertical adjustment of a tongue suppressor relative to a bite block. In addition, they comprise means for selective angular and horizontal movement of a tongue suppression relative to a bite block.

The tongue suppressor 60 further includes a retention arm 64 configured so as to extend over the surface of the patient's tongue in order to maintain the tongue in a suppressed orientation beneath the tongue suppressor 60 in the bottom of the patient's mouth. In addition, the tongue suppressor 60 may include a flange or other protrusion 66 extending from the retention arm 64 distal to the insertion peg 62 in order to provide an additional tongue suppression feature. The interface between the retention arm 64 and 66 may be curved so as to conform to the curvature of the patient's tongue between the top and side of the tongue so as to provide maximum comfort.

Figure 7:
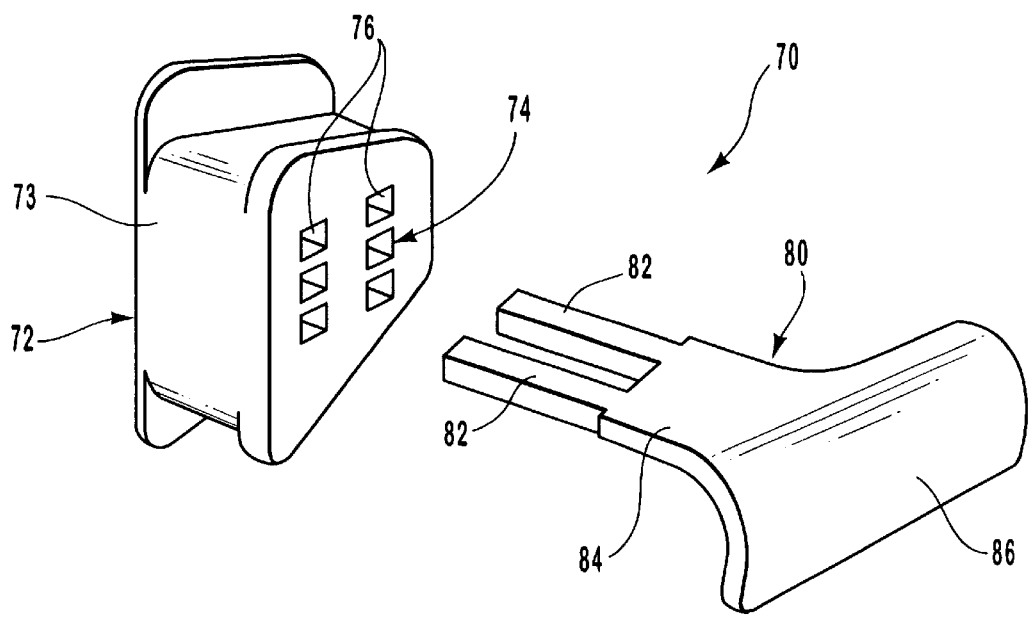
FIG. 7 is a perspective view of an alternative embodiment of a tongue suppressing bite block in which the tongue suppressor includes prongs designed to engage corresponding recesses within the bite block.

FIG. 7 depicts another embodiment of a tongue suppressing bite block system 70 according to the invention. The tongue suppressing bite block system 70 comprises a bite block 72 having a body 73, which includes a plurality of adjustment recesses 74 comprising individual pairs or sets of recesses 76, and a tongue suppressor 80. The tongue depressor 80 includes a retention arm 84 and a pair or set of adjustment prongs 82 that are sized and configured to be selectively received within desired one of the pairs or sets of adjustment recesses 76 within the bite block body 73. The tongue suppressor 80 further includes a flange 86 that functions as described elsewhere in the specification. The adjustment prongs 82 and adjustment recesses 74 comprise adjustment means for selective lateral and vertical adjustment of a tongue suppressor relative to a bite block.

In one embodiment, the components of tongue suppressing bite block systems according to the invention may be formed from flexible, resilient materials such as rubber, latex and other elastomeric materials that can be temporarily deformed by exerting a deformation force thereto but which return to their original shape upon removal of the deformation force. Various polymers or other materials may be selected for accommodation of stiffness and flexibility as may be structurally required. All or part of the tongue-suppressing bite block systems according to the invention may be made from harder and more rigid materials such as thermoset materials, thermoplastic materials, foams and other plastics or composite materials, wood, metal, ceramics, fiberglass and the like. The components of the tongue-suppressing bite block systems may be formed using various techniques, such as injection molding, blow molding, tumble molding, casting, vacuum forming, machining and the like.

The tongue suppressing bite block systems according to the invention may comprise higher quality materials that are durable and autoclavable (or otherwise sterilizable) in order to provide a device that can be reused a number of times. In the alternative, the tongue suppressing bite block systems may be formed from inexpensive materials that allow them to be disposable and intended only for a single use. Disposability eliminates risks associated with improper sterilization between uses. In either case, the tongue suppressing bite block systems of the invention may be advantageously sterilized at the point of manufacture and packaged in a sterile manner so as to maintain sterility until opened for use.

In order to mask the unpleasant taste that may be detected when using certain materials in the manufacture of the tongue suppressing bite block systems, the apparatus may be coated or infused with one or more flavoring agents so as to provide a more pleasant taste. Examples include bubble gum, mint, grape, cherry, chocolate and the like in order to increase the palatibilty of the device when inserted into the patient's mouth.

Figure 8A:
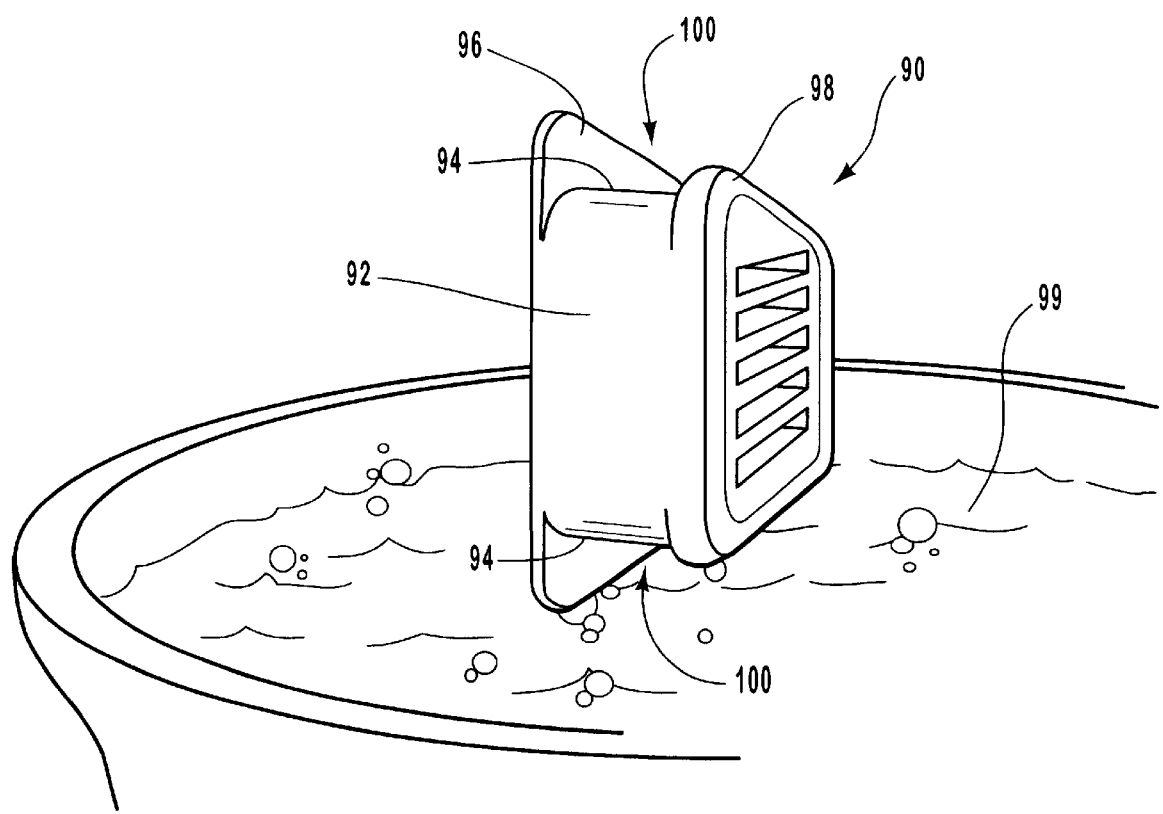

Reference is now made to FIGS. 8A–8D. These figures depict a bite block 90 comprising a body 92 sized and configured so as to fit between the upper and lower teeth of a patient's mouth while in an open position. The bite block body 92 is advantageously angled in order to provide surfaces 94 that make continuous contact with the patient's teeth when in position between the teeth. Extending from upper and lower sides of the bite block 92 are an outer shoulder 96 and an inner shoulder 98 that define upper and lower channels 100 into which a patient's teeth 102 (FIG. 8B) can be inserted to engage the surfaces 94 of the bite block body 92. FIG. 8A depicts the bite block 90 being inserted into boiling water 99, although it may be heated using other means (e.g., by a heat lamp, hot air blower, torch, microwave oven, and the like).

At least a portion of the bite block 90 advantageously comprises an impression material that is plastically deformable at a predetermined temperature or temperature range so that the surfaces 94 of the bite block body 92 can form an impression 104 of the patient's teeth 102 in contact therewith, as illustrated more particularly in FIGS. 8B and 8C. The term "impression material" broadly includes any material capable of being plastically deformed to a predetermined temperature or temperature range, and/or while in an uncured or semi-cured state.

Figure 13:
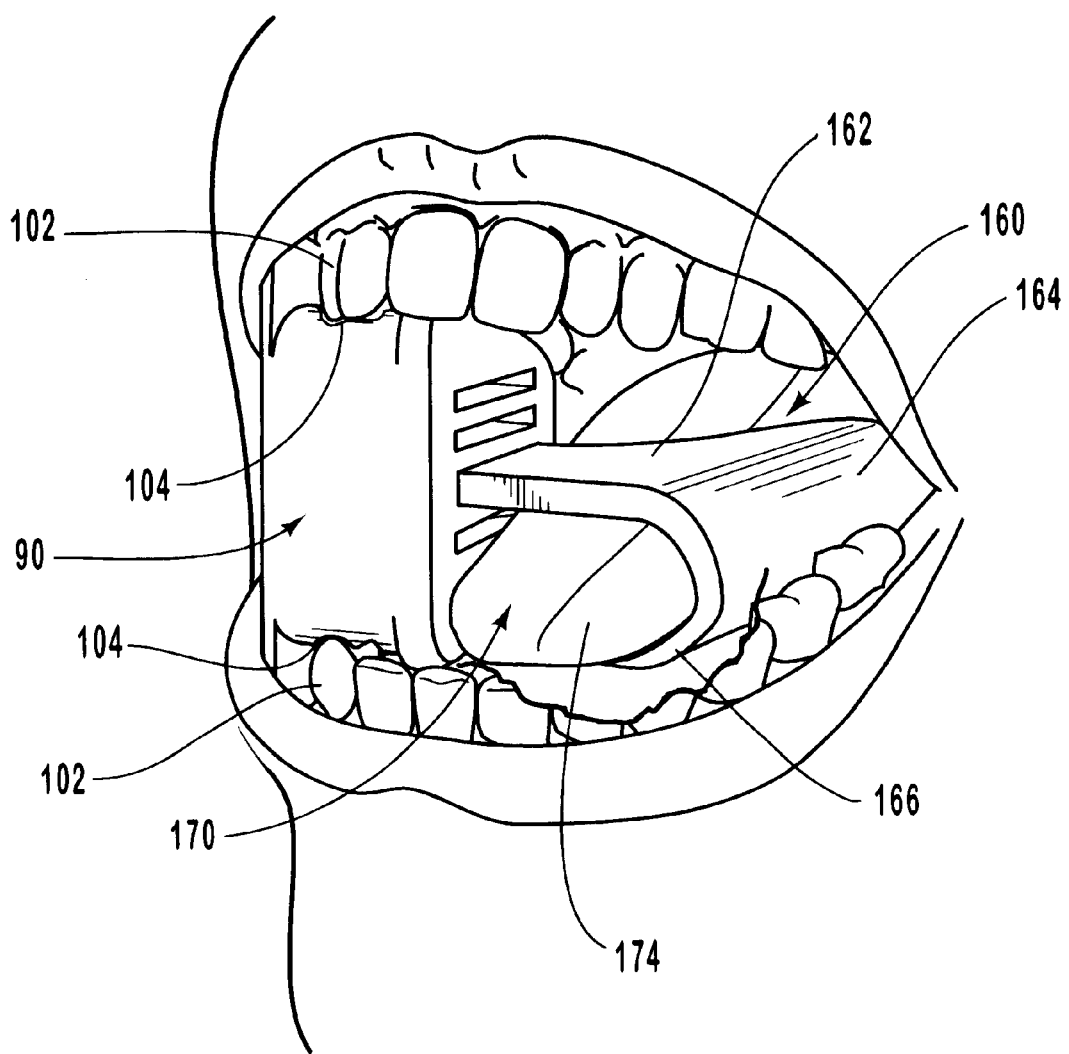
FIG. 13 depicts a tongue suppressing bite block system as in of FIG. 12 inserted within a patient's mouth.

FIG. 8C depicts a dental impression 104 comprising tooth indentations 106 corresponding to the portion of the patient's teeth 102 that contact the surfaces 94 of the bite block 92. Forming a customized bite block in this manner improves patient comfort by providing a more precise fit with the patient's teeth in contact therewith. The customized bite block is also less likely to slip out from between the patient's teeth due to the mechanical interaction of the dental impression 104 and the patient's teeth 102 when used to hold a patient's mouth open, as illustrated in FIG. 13. Patient comfort may also be increased because a customized bite block reduces the need to tightly wedge the bite block between the patient's teeth, as is often necessary using conventional bite blocks, in order to maintain it in the proper position.

It is within the scope of the invention to mold the bite block 90 from a single material that is plastically deformable at the predetermined temperature or temperature range. In the alternative, it is within the scope of invention to provide a bite block that comprises a plastically deformable material at a predetermined depth below and including the surfaces of the bite block body and a non-plastically deformable material in the middle. As illustrated in FIG. 8D, a bite block 90' is shown that includes a substantially rigid body region 108 that is not plastically deformable and an impression region 109 comprising a plastically deformable material. The impression region 109 may have any desired depth in order to provide a sufficient quantity of the plastically deformable material so as to yield a suitable dental impression. In a preferred embodiment, the impression region 109 comprising the plastically deformable material may have a depth in a range of about 0.5 mm to about 1.5 cm, more preferably in a range from about 2 mm to about 1 cm, and most preferably in a range from about 3 mm to about 7 mm.

The plastically deformable impression material may comprise any suitable material that is able to make and retain an impression of the patient's teeth. The term "plastically deformable" describes a material that is able to be deformed and that is at least partially nonresilient so that it will not return to its original shape upon removal of the external force used to plastically deform the material. The term "plastically deformable" should be contrasted with terms such as "resilient" or "elastic", which describe materials that can be temporarily deformed by application of an external force but which will return to the original shape upon removal of the external force as a result of internal molecular and/or mechanical forces.

The plastically deformable material may be capable of plastic deformation at room temperature (generally understood to be 20–25° C.), or it may be selected so as to preferably become plastically deformable at a temperature in a range of about 40° C. to about 110° C., more preferably in a range of about 50° C. to about 90° C., and most preferably in a range of about 55° C. to about 90° C. The plastically deformable materials typically remain plastically deformable above the temperature at which they initially become plastically deformable, although at higher temperatures they may become liquid or they may decompose or char.

In the alternative, instead of an impression material that softens or hardens in response to changes in temperature, it is within the scope of the invention to use impression materials that are light, heat or chemical curable so that they can be initially plastically deformable (e.g., at or above body temperature) but that, upon curing, become nonplastically deformable. There are a wide range of curable resins, alginates and other substances used to make composites, sealants, temporary cements, dental impressions, and the like in the dental art. One of ordinary skill in the art will be able to select or modify any known curable resin known in the art in order to yield a bite block having a desired level of initial plasticity and final hardness, durability or resilience.

Impression materials that are plastically deformable at a temperature greater than body temperature generally include any thermoplastic material that has a softening temperature or range greater than body temperature but which is not plastically deformable at body temperature. Examples include ethylene-vinyl acetate copolymers, other vinyl polymers, polycaprolactone, other polyesters, polyethylene, ultra low density polyethylene, other polypropylene, polyalkylenes, polyurethanes, and polyesters, including open and closed cell foams and nonfoamed polymers.

Examples of impression materials that are plastically deformable at body temperature include a wide range of waxes, gums and low softening temperature polymers, such as polyesters.

Examples of impression materials that are curable so as to be initially plastically deformable but then become either rigid or resilient upon curing include alginates, acrylates, methacrylates, silicones, epoxies, and polyethers.

Some impression materials that become plastically deformable at a temperature or temperature range above body temperature may be substantially rigid and non deformable at body temperature. Other impression materials that are plastically deformable at elevated temperatures may become resilient and elastic when cooled to body temperature so that the dental impression may be temporarily deformed through application of external force but then restored to its original shape upon removal of the external force. Materials that are initially plastically deformable but become resilient at lower temperatures or upon curing provide the most comfort. Examples include ultra low density polyethylene, ethylene-vinyl acetate copolymers, blends of such polymers and more rigid polymers, alginates, and various open and closed cell foams.

The exemplary bite blocks 90, 90' depicted in FIGS. 8A–8D includes outer and inner shoulders 96, 98 having opposing interior walls that are substantially parallel so as to bound the tooth engagement surfaces 94, 94' on either side. It will be appreciated, however, that the outer and inner shoulders 96, 98 may have any desired configuration, such as nonparallel configurations, as desired to yield a desired bite block 90. As shown in FIGS. 9A–10D, the interior walls of the inner and outer shoulders may be configured so as to converge in a direction toward the tooth engagement surfaces of the bite block body in order for the patient's teeth to engage the interior walls of the outer and inner shoulders.

Figure 9A:
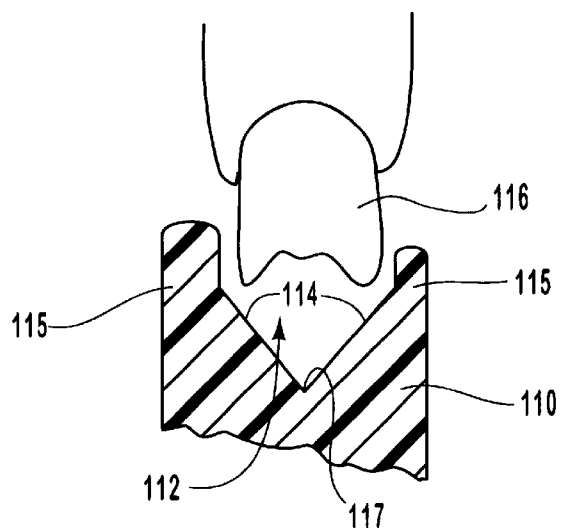
FIGS. 9A–9C depict an alternative embodiment of a customizable bite block incorporating a V-shaped channel for registering patient dentition.
Figure 9B:
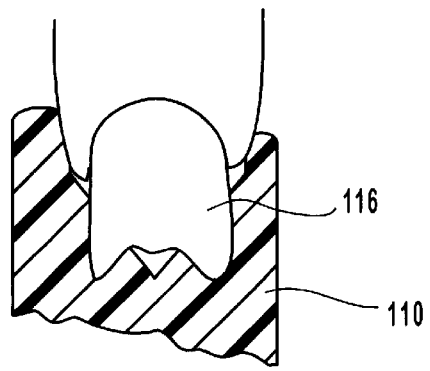
Figure 9C:
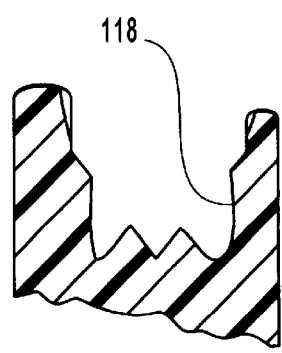

FIGS. 9A–9C depict an alternative embodiment of a bite block according to the invention, particularly a portion of a bite block 110 that includes a V-shaped channel 112 defined by interior walls 114 of shoulders 115 that converge together. The V-shaped channel 112 is sufficiently wide at its upper end to receive a patient's tooth 116 therebetween, but that sufficiently narrows towards an apex 117 so that an impression 118 can be formed in the interior walls 114 defining the V-shaped channel 112, as illustrated in FIGS. 9B and 9C. In this embodiment, at least a portion of the shoulders 115 in the vicinity of the interior walls 114 comprise an impression material that is plastically deformable at a predetermined temperature and/or prior to curing as more particularly described above.

Figure 10A:
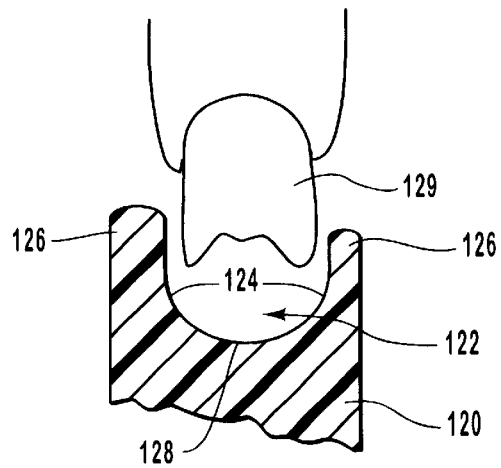
FIGS. 10A–10D depict other customizable bite blocks having varying shaped channels for registering patient dentition.

FIG. 10A depicts a portion of a bite block 120 that includes a U-shaped channel 122 defined by interior walls 124 of shoulders 126 that are curved so as to converge towards a bottom 128 of the U-shaped channel 122. This allows a tooth 129 to form an impression within the interior walls 124 when in a plastically deformable state.

Figure 10B:
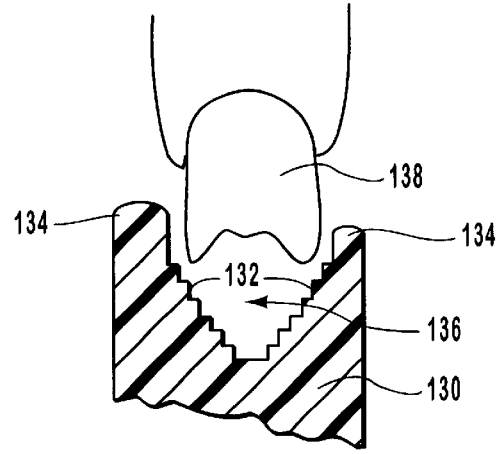

FIG. 10B depicts a portion of a bite block 130 that includes stepped interior walls 132 of shoulders 134 that define a converging impression channel 136. In this manner, a tooth 138 can form an impression within the impression channel 136 when in a plastically deformable state.

Figure 10C:
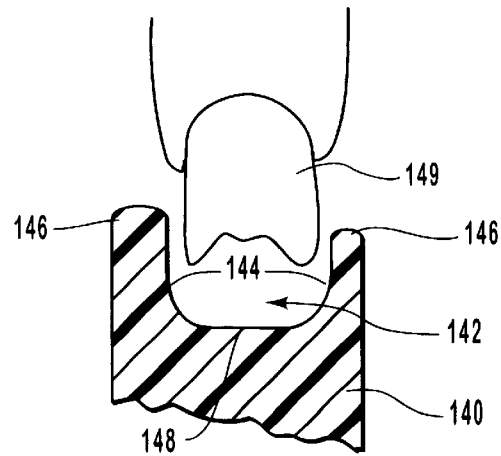

FIG. 10C depicts a portion of a bite block 140 according to the invention that includes a wide U-shaped channel 142 defined by interior walls 144 of shoulders 146 that are substantially parallel near the opening but which converge towards a bottom 148 of the wide U-shaped channel 142. This allows a tooth 149 to form an impression within the interior walls 142 at or near the bottom 148 of the wide U-shaped channel 142 when in a plastically deformable state.

Figure 10D:
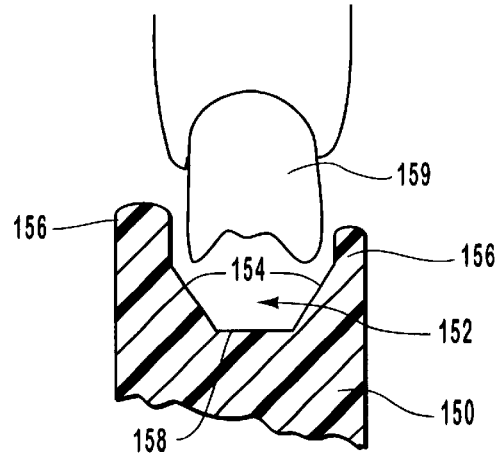

FIG. 10D depicts a portion of a bite block 150 according to the invention that includes an impression channel 152 defined by interior walls 154 of shoulders 156 that are substantially parallel near the opening but which angle towards each other but do not converge at a bottom 158 of the impression channel 152. This allows a tooth 159 to form an impression within the angled portion of the interior walls 154 while in a plastically deformable state.

As illustrated in FIGS. 9A–10D there are a number of shapes or configurations in which the interior walls of the shoulders extending from a bite block body can at least partially converge so as to form an impression surface for making an impression of the patient's teeth. The inner walls may converge, for example by being angled, stepped, curved, or the like. Based on the teachings contained herein, one of ordinary skill in the art will be able to modify any of the particular configurations of impression surfaces described herein, or create new ones, to create a desired impression surface tailored to specified needs or tastes. Such modifications or new designs are within the scope of the invention.

Figure 11:
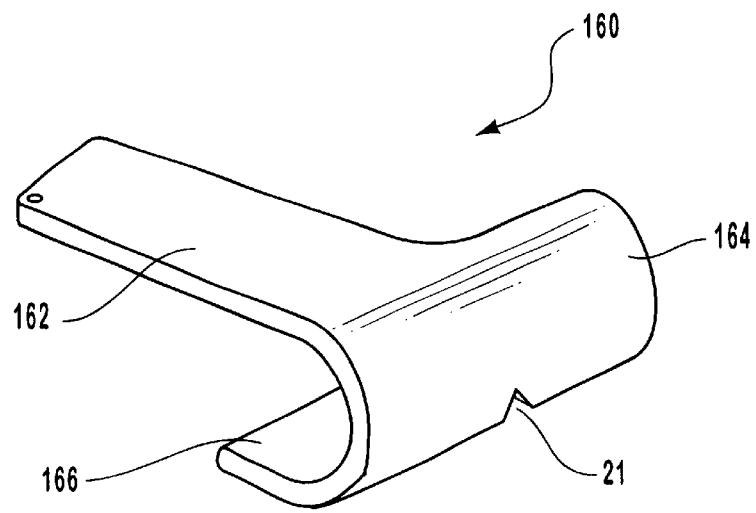
FIG. 11 depicts an anatomically shaped tongue suppressor for use with a bite block.
Figure 12:
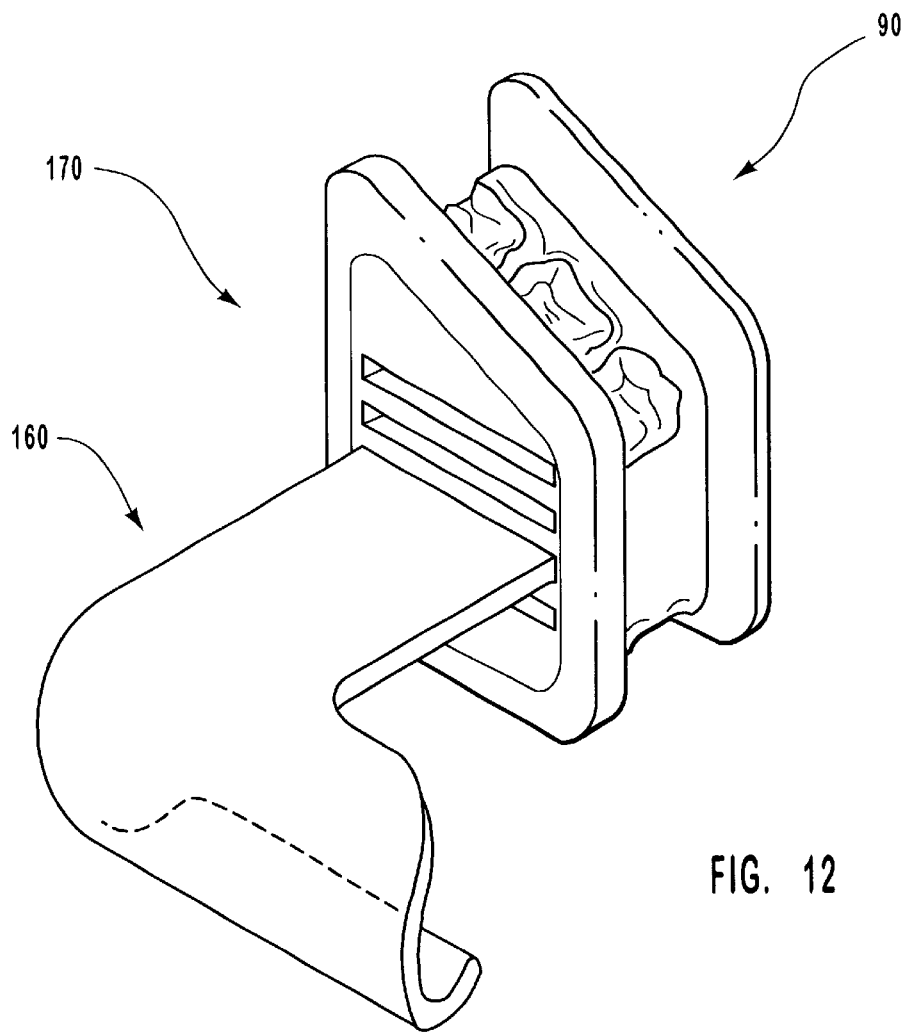
FIG. 12 depicts a tongue suppressing bite block system comprising a customized bite block that includes an impression of a patient's teeth and an anatomical tongue suppressor as in FIG. 11.

Attention is now directed to FIGS. 11–13, which depict an anatomically configured tongue suppressor that is able to cradle the patient's tongue in order to more comfortably and reliably maintain the tongue in a desired suppressed orientation when in use.

As more particularly illustrated in FIG. 11, an anatomical tongue suppressor 160 includes a retention arm 162 that is configured so that at least a portion thereof extends transversely across the patient's tongue (not shown) when in use. Disposed at an end of the retention arm 162 is a curved side flange 164 that is configured to engage a side of the patient's tongue when in use and that includes a sublingual portion 166 that curves around and under the patient's tongue in order to cradle the patient's tongue and more reliably and comfortably retain the tongue in a suppressed orientation during use.

The anatomical tongue suppressor 160 may be used in conjunction with any bite block known in the art. Through routine testing and design change, one of ordinary skill in the art will be able to provide a configuration of a retention arm 162, and any auxiliary or modified structures, in order for the anatomical tongue suppressor 160 (or similar tongue suppressors like unto it) to mechanically engage any bite block known in the art.

FIG. 12 illustrates an embodiment in which the anatomical tongue suppressor 160 is combined with the customizable bite block 90 depicted in FIG. 8C in order to yield an anatomical bite block system 170. Nevertheless, it will be appreciated that the anatomical tongue suppressor 160, or similar tongue suppressors like unto it, can be used with any of the bite blocks disclosed herein or other bite blocks known in the art.

FIG. 13 depicts an anatomical bite block system 170 used in maintaining a patient's mouth in a desired open position. In this embodiment, the anatomical tongue suppressor 160, more particularly retention arm 162, extends transversely across the top of the patient's tongue 174, with the curved side flange 164 and sublingual portion 166 curving around and under the patient's tongue 174 in order to cradle it and more comfortably and reliably maintain it in a desired suppressed orientation.

The bite block 90 includes an impression 104 of the patient's teeth 102 in order to form an anatomically correct fit with the patient's teeth 102. This has the effect of more reliably maintaining the bite block 90 between the patient's teeth 102 when in use and reducing the tendency of the bite block 90 to inadvertently slip out from between the teeth 102. Due to this safety feature, the bite block 90 is more comfortable to the patient because the anatomical fit reduces orthodontic forces that would otherwise bear against the patient's teeth. In addition, it may be possible to insert the bite block 90 between the patient's teeth with less force than may be otherwise required when using conventional, non-customized bite blocks.

Figure 14A:
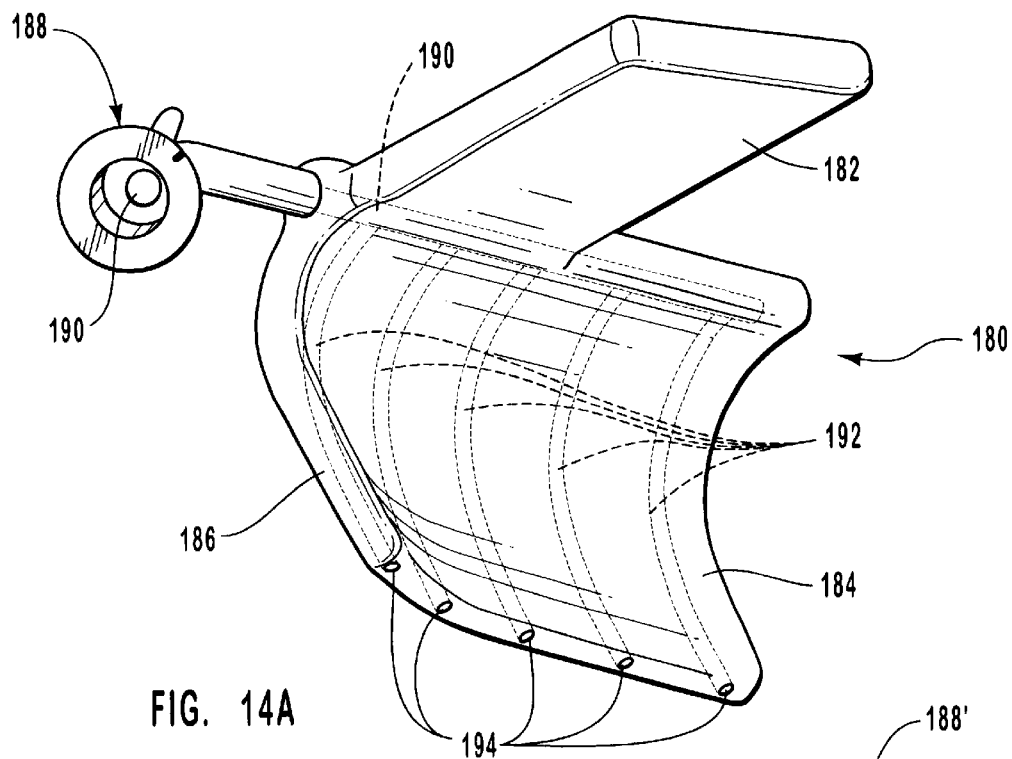
FIGS. 14A–14B depict alternative embodiments of an anatomically shaped tongue suppressor that includes a saliva aspiration port.
Figure 14B:
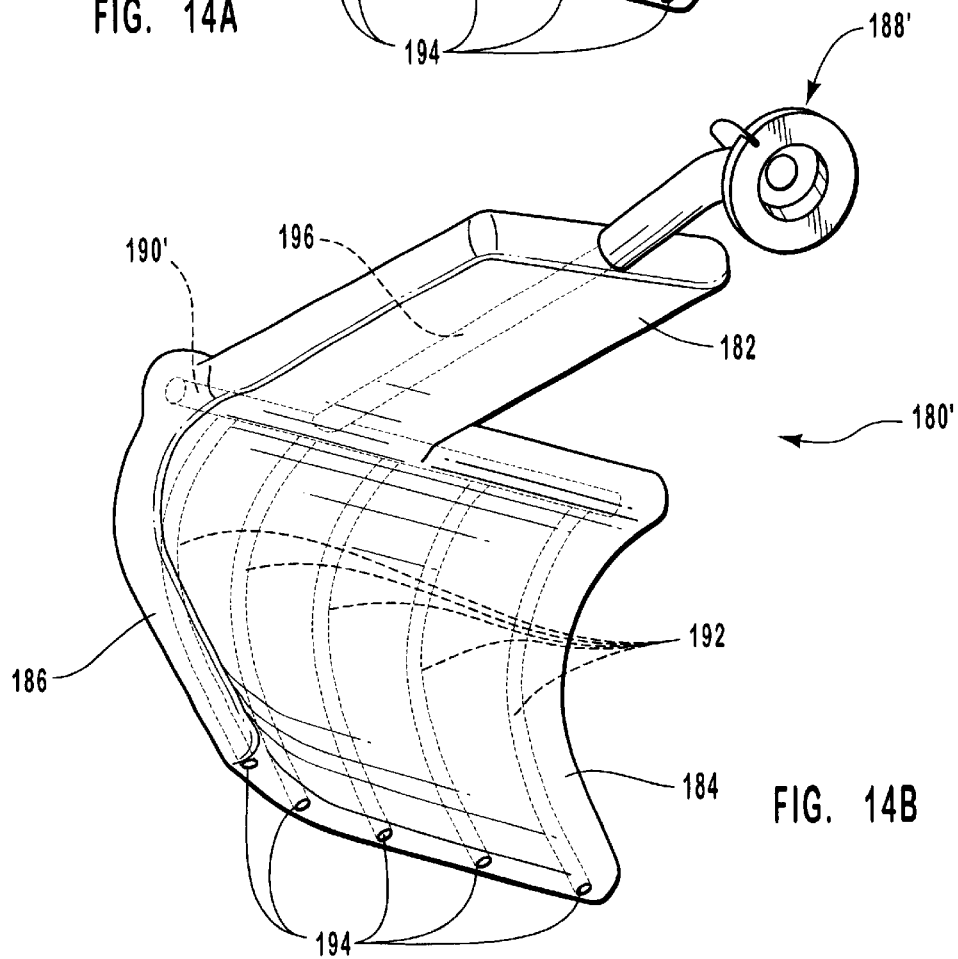

FIGS. 14A and 14B depict other alternative embodiments of a tongue suppressor. In particular, FIG. 14A illustrates a tongue suppressor 180 comprising a retention arm 182 and a curved side flange 184. The curved side flange 184 is configured so as to curve around and under the patient's tongue (not shown) when in use. Curved side flange 184 includes a forward curved section 186 configured so as to more anatomically engage the curved tip of the patient's tongue when in use. The tongue suppressor 180 further includes a saliva aspiration port 188 attached to a side of the curved side flange 184. The saliva aspiration port 188 is hollow such that it includes an aspiration lumen 190 that branches into or communicates with one or more secondary aspiration lumens 192 that pass through the curved side flange 184 and terminate at one or more corresponding saliva aspiration holes 194 disposed in, or along an edge of, a side of the curved side flange 184. When in use, a dental aspirator (not shown) can be attached to, or otherwise engaged with, the saliva aspiration port 188 in order to aspirate saliva within the patient's mouth. The aspiration vacuum is transmitted by the saliva aspiration port 188 through the aspiration lumen 190 and through the secondary aspiration lumens 192 to saliva aspiration holes 194. This allows a dentist or other dental practitioner to evacuate saliva from the patient's mouth without removing or interfering with the bite block (not shown).

FIG. 14B depicts a variation of a tongue suppressor 180' that is similar to the tongue suppressor 180 depicted in FIG. 14A, except that the saliva aspiration port 188' is located at an end of the retention arm 182 distal to the curved side flange 184. In this embodiment, an auxiliary aspiration lumen 196 communicates between the saliva aspiration port 188' and the aspiration lumen 190'.

Figure 15:
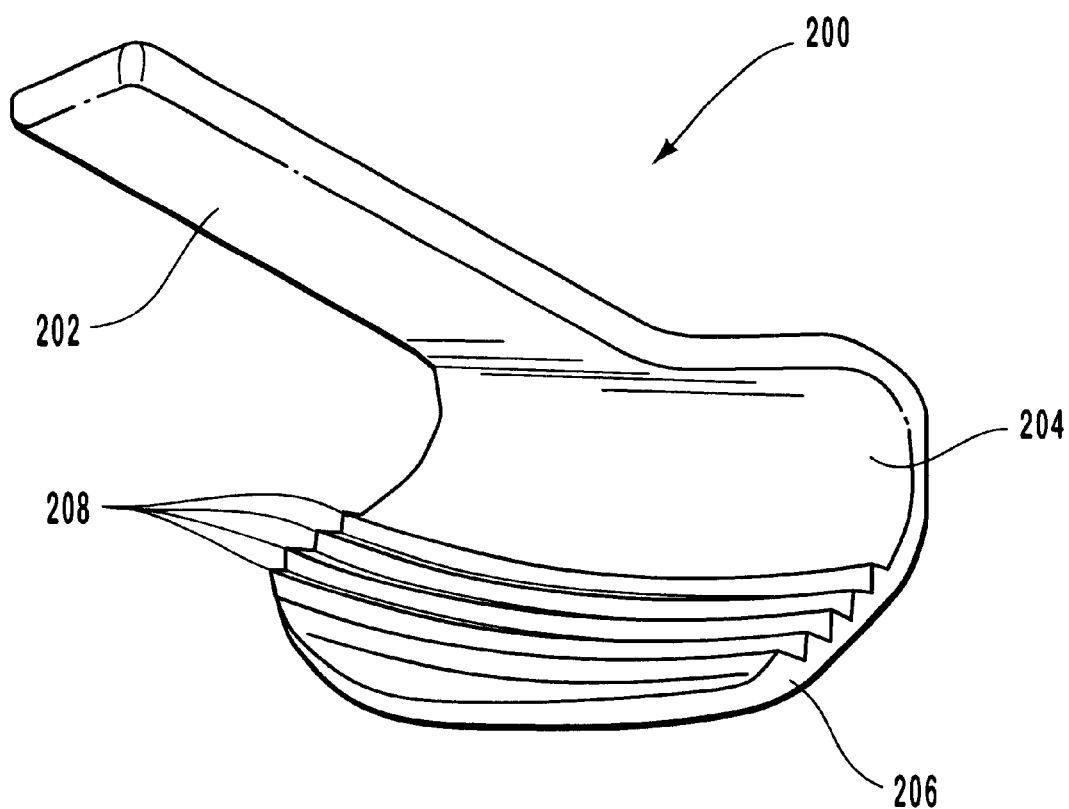
FIG. 15 depicts an anatomically shaped tongue suppressor that includes a plurality of ridges on a side adjacent to the patient's tongue when in use.

FIG. 15 depicts an alternative embodiment of a tongue suppressor 200 comprising a retention arm 202 connected to a curved side flange 204. The curved side flange 204 further includes a sublingual portion 206 and a plurality of engagement ridges 208 that are configured so as to frictionally or mechanically engage a portion of the patient's tongue when in use in combination with a bite block (not shown). The engagement ridges 208 assist the tongue suppressor 200 in maintaining the patient's tongue (not shown) in a desired suppressed configuration relative to the bite block (not shown).

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A customizable bite block for use in maintaining a patient's mouth in an open position while providing unobstructed access to some of the patient's teeth during a dental procedure, comprising:
    a bite block body sized and configured so that the bite block fits entirely within one side of the patient's mouth when in use so as to provide unobstructed access to at least some teeth on an opposite side of the patient's mouth;
    an upper surface disposed on an upper side of said bite block body and adapted for engagement with a portion of the patient's upper teeth on the one side of the patient's mouth when the bite block is positioned within the patient's mouth; and
    a lower surface disposed on a lower side of said bite block body and adapted for engagement with a portion of the patient's lower teeth on the one side of the patient's mouth when the bite block is positioned within the patient's mouth,
    at least one of the upper and lower surfaces comprising an impression material that is plastically deformable (i) at or above a predetermined temperature or temperature range or (ii) prior to curing in order to make an impression of a portion of the patient's teeth on the one side of the patient's mouth.

2. A customizable bite block as defined in claim 1, at least a portion of the bite block body comprising the impression material.

3. A customizable bite block as defined in claim 1, at least a portion of the bite block body comprising a rigid material that is generally non-plastically deformable at the predetermined temperature or temperature range.

4. A customizable bite block as defined in claim 1, the upper and lower surfaces and the upper and lower sides of the bite block body comprising the impression material to a depth in a range of about 0.5 mm to about 1.5 cm.

5. A customizable bite block as defined in claim 1, the upper and lower surfaces and the upper and lower sides of the bite block body comprising the impression material to a depth in a range of about 2 mm to about 1 cm.

6. A customizable bite block as defined in claim 1, the upper and lower surfaces and the upper and lower sides of the bite block body comprising the impression material to a depth of about 3 mm to about 7 mm.

7. A customizable bite block as defined in claim 1, the impression material comprising at least one component selected from the group consisting of ethylene-vinyl acetate copolymers, polycaprolactone, polyesters, polyethylene, polypropylene, ultra low density polyethylene, polyalkylenes, waxes, gums, polyurethanes, polyesters, open cell foams, and closed cell foams.

8. A customizable bite block as defined in claim 1, the predetermined temperature or temperature range at which the impression material is plastically deformable being greater than room temperature so that the impression material is substantially non-plastically deformable at room temperature.

9. A customizable bite block as defined in claim 1, the predetermined temperature or temperature range at which the impression material is plastically deformable being greater than body temperature so that the impression material is substantially non-plastically deformable at body temperature.

10. A customizable bite block as defined in claim 9, the predetermined temperature being between about 40° C. to about 110° C.

11. A customizable bite block as defined in claim 9, the predetermined temperature being between about 50° C. to about 90° C.

12. A customizable bite block as defined in claim 9, the predetermined temperature being between about 55° C. to about 90° C.

13. A customizable bite block as defined in claim 1, the impression material being plastically deformable at room temperature.

14. A customizable bite block as defined in claim 1, the impression material being plastically deformable at body temperature.

15. A customizable bite block as defined in claim 1, the impression material being resiliently deformable at room temperature.

16. A customizable bite block as defined in claim 1, the impression material being resiliently deformable at body temperature.

17. A customizable bite block as defined in claim 1, the impression material being at least partially non-resilient so that once an impression of the patient's teeth is made at least a portion of the impression will persist indefinitely absent application of a force sufficient to plastically deform the impression.

18. A customizable bite block as defined in claim 1, the impression material being at least partially non-resilient at a temperature at which the impression material is plastically deformable.

19. A customizable bite block as defined in claim 18, the impression material being at least partially resilient below a temperature at which the impression material initially becomes plastically deformable so that the impression, if deformed by application of a force, is at least partially restored upon relaxation of the force.

20. A customizable bite block as defined in claim 1, the impression material comprising a curable material that is initially plastically deformable but which becomes non-plastically deformable upon curing.

21. A customizable bite block as defined in claim 20, the impression material comprising at least one of a light, heat, or chemically curable material.

22. A customizable bite block as defined in claim 20, the impression material comprising at least one of an alginate, acrylate, methacrylate, silicone, epoxy or polyether.

23. A customizable bite block as defined in claim 1, further comprising:
    a pair of upper shoulders extending from the upper side of the bite block body and defining an upper channel within which the upper surface is at least partially disposed; and
    a pair of lower shoulders extending from the lower side of the bite block body and defining a lower channel within which the lower surface is at least partially disposed.

24. A customizable bite block as defined in claim 23, at least one of the upper or lower channels being bounded by substantially parallel opposing interior walls of corresponding upper or lower shoulders.

25. A customizable bite block as defined in claim 23, at least one of the upper or lower channels being bounded by opposing interior walls of corresponding upper or lower shoulders, at least a portion of the interior walls being configured so that they at least partially converge toward a respective upper or lower side of the bite block body.

26. A customizable bite block as defined in claim 25, the upper or lower shoulders defining a corresponding channel that is substantially V-shaped, U-shaped, or step-walled.

27. A customizable bite block as defined in claim 25, at least a portion of the interior walls comprising the impression material.

28. A customizable bite block as defined in claim 1, at least one of the upper or lower surfaces including an impression of a portion of the patient's teeth, the bite block being adapted so as to maintain the impression after removing the bite block from the patient's mouth.

29. A customizable bite block as defined in claim 28, the impression assisting in retaining the bite block within the patient's mouth during a dental procedure.

30. A customizable bite block as defined in claim 28, the bite block being sized and configured so as to provide for a desired degree of opening of the patient's mouth.

31. A customizable bite block as defined in claim 1, further including a tongue suppressor attached to the bite block body and oriented so as maintain the patient's tongue within a confined region of the patient's oral cavity when the bite block is positioned within the patient's mouth.

32. A customizable bite block as defined in claim 31, the tongue suppressor being adjustably attached to the bite block body in a manner so as to permit at least one of lateral or vertical adjustments of the tongue suppressor relative to the bite block.

33. A customizable bite block as defined in claim 31, the tongue suppressor being anatomically configured so as to wrap around and cover at least a portion of the top, side and underside of the patient's tongue.

34. A customizable bite block for use in maintaining a patient's mouth in an open position while providing unobstructed access to some of the patient's teeth during a dental procedure, comprising:
   a bite block body sized and configured so that the bite block fits entirely within one side of the patient's mouth when in use so as to provide unobstructed access to at least some teeth on an opposite side of the patient's mouth;
   a pair of upper shoulders extending from an upper side of the bite block body and defining an upper channel comprising an upper impression surface adapted for engagement with a portion of the patient's upper teeth on the one side of the patient's mouth when the bite block is positioned within the patient's mouth; and
   a pair of lower shoulders extending from a lower side of the bite block body and defining a lower channel comprising a lower impression surface adapted for engagement with a portion of the patient's lower teeth on the one side of the patient's mouth when the bite block is positioned within the patient's mouth,
   at least the upper and lower impression surfaces comprising an impression material that initially becomes plastically deformable when heated to above room temperature and below about 110° C. in order to make an impression of a portion of the patient's teeth on the one side of the patient's mouth and then at least partially retain the impression when cooled to room temperature.

35. A customizable bite block as defined in claim 34, the upper and lower channels being bounded by substantially parallel opposing interior walls of corresponding upper or lower shoulders.

36. A customizable bite block as defined in claim 34, the upper and lower channels being bounded by interior walls of corresponding upper or lower shoulders, at least a portion of the interior walls being configured so as to at least partially converge toward a respective upper or lower side of the bite block body.

37. A customizable bite block as defined in claim 36, the upper or lower shoulders defining a corresponding channel that is at least partially V-shaped or U-shaped.

38. A customizable bite block as defined in claim 34, further including a tongue suppressor attached to the bite block body and oriented so as maintain the patient's tongue within a confined region of the patient's oral cavity when the bite block is positioned within the patient's mouth.

39. A customizable bite block as defined in claim 38, the tongue suppressor being adjustably attached to the bite block body in a manner so as to permit at least one of lateral or vertical adjustments of the tongue suppressor relative to the bite block.

40. A customizable bite block as defined in claim 34, the bite block body having an exterior region comprising a material that is plastically deformable at a temperature in a range of about 40° C. to about 110° C. and an interior region that is not plastically deformable within the temperature range.

41. A customizable bite block for use in maintaining a patient's mouth in an open position while providing unobstructed access to some of the patient's teeth during a dental procedure, comprising:
   a bite block body sized and configured so that the bite block fits entirely within one side of the patient's mouth when in use so as to provide unobstructed access to at least some teeth on an opposite side of the patient's mouth;
   a pair of upper shoulders extending from an upper side of the bite block body and comprising first opposing interior walls defining an upper channel comprising an upper impression surface adapted for engagement with a portion of the patient's upper teeth on the one side of the patient's mouth when the bite block is positioned within the patient's mouth, at least a portion of the first opposing interior walls being configured so as to at least partially converge toward the upper side of the bite block body; and
   a pair of lower shoulders extending from a lower side of the bite block body and comprising second opposing interior walls defining a lower channel comprising a lower impression surface adapted for engagement with a portion of the patient's lower teeth on the one side of the patient's mouth when the bite block is positioned within the patient's mouth, at least a portion of the second opposing interior walls being configured so as to at least partially converge toward the lower side of the bite block body,
   at least a portion of the first and second opposing interior walls comprising an impression material that is plastically deformable at or above room temperature in order to make an impression of a portion of the patient's teeth on the one side of the patient's mouth.

42. A customizable bite block as defined in claim 41, the impression material initially becoming plastically deformable at a temperature greater than room temperature and less than about 110° C. so that the impression material is substantially non-plastically deformable at room temperature.

43. A customizable bite block as defined in claim 41, the impression material comprising a curable material that becomes substantially non-plastically deformable upon curing.

44. A customizable bite block as defined in claim 41, further including a tongue suppressor attached to the bite block body and oriented so as maintain the patient's tongue within a confined region of the patient's oral cavity when the bite block is positioned within the patient's mouth.

45. A customizable bite block as defined in claim 44, the tongue suppressor being adjustably attached to the bite block body in a manner so as to permit at least one of lateral or vertical adjustments of the tongue suppressor relative to the bite block.

46. A method of making a customized bite block for use in maintaining a patient's mouth in an open position while providing unobstructed access to some of the patient's teeth during a dental procedure, the method comprising:

providing a bite block having an upper surface adapted to engage a portion of the patient's upper teeth and a lower surface adapted to engage a portion of the patient's lower teeth;

heating the bite block to a temperature at which at least one of the upper or lower surfaces is plastically deformable;

placing the bite block into one side of the patient's mouth so that an opposite side of the patient's mouth remains unobstructed by the bite block;

causing at least a portion of the patient's teeth on the one side of the patient's mouth to make an impression in at least one of the upper or lower surfaces of the bite block; and cooling the bite block in order to at least partially set the impression.

47. A customized bite block manufactured according to the method of claim 46.

48. A method of making a customized bite block for use in maintaining a patient's mouth in an open position while providing unobstructed access to some of the patient's teeth during a dental procedure, the method comprising:

providing a bite block having an upper surface adapted to engage a portion of the patient's teeth and a lower surface adapted to engage a portion of the patient's lower teeth, at least one of the upper and lower surfaces comprising an impression material that is plastically deformable at room temperature;

placing the bite block into one side of the patient's mouth so that an opposite side of the patient's mouth remains unobstructed by the bite block; and causing at least a portion of the patient's teeth on the one side of the patient's mouth to make an impression in at least one of the upper or lower surfaces of the bite block.

49. A customized bite block manufactured according to the method of claim 48.

50. A method according to claim 48, the impression material comprising a curable material, the method further comprising curing the impression material in order to render it substantially non-plastically deformable.

51. A customized bite block manufactured according to the method of claim 50.

52. A customizable bite block for use in maintaining a patient's mouth in an open position, comprising:

a bite block body sized and configured so that the bite block is positionable within the patient's mouth;

an upper surface disposed on an upper side of said bite block body and adapted for engagement with a portion of the patient's upper teeth when the bite block is positioned within the patient's mouth;

a lower surface disposed on a lower side of said bite block body and adapted for engagement with a portion of the patient's lower teeth when the bite block is positioned within the patient's mouth, at least one of the upper and lower surfaces comprising an impression material that is plastically deformable (i) at or above a predetermined temperature or temperature range or (ii) prior to curing in order to make an impression of a portion of the patient's teeth; and a tongue suppressor attached to the bite block body and oriented so as maintain the patient's tongue within a confined region of the patient's oral cavity when the bite block is positioned within the patient's mouth.

53. A customizable bite block as defined in claim 52, the tongue suppressor being adjustably attached to the bite block body in a manner so as to permit at least vertical adjustment of the tongue suppressor relative to the bite block.

54. A customizable bite block for use in maintaining a patient's mouth in an open position, comprising:

a bite block body sized and configured so that the bite block is positionable within the patient's mouth;

a pair of upper shoulders extending from an upper side of the bite block body and defining an upper channel comprising an upper impression surface adapted for engagement with a portion of the patient's upper teeth when the bite block is positioned within the patient's mouth;

a pair of lower shoulders extending from a lower side of the bite block body and defining a lower channel comprising a lower impression surface adapted for engagement with a portion of the patient's lower teeth when the bite block is positioned within the patient's mouth, at least the upper and lower impression surfaces comprising an impression material that initially becomes plastically deformable when heated to above room temperature and below about 110° C. in order to make an impression of a portion of the patient's teeth and then at least partially retain the impression when cooled to room temperature; and a tongue suppressor attached to the bite block body and oriented so as maintain the patient's tongue within a confined region of the patient's oral cavity when the bite block is positioned within the patient's mouth.

55. A customizable bite block as defined in claim 54, the tongue suppressor being adjustably attached to the bite block body in a manner so as to permit at least vertical adjustment of the tongue suppressor relative to the bite block.

56. A customizable bite block for use in maintaining a patient's mouth in an open position, comprising:

a bite block body sized and configured so that the bite block is positionable within the patient's mouth;

a pair of upper shoulders extending from an upper side of the bite block body and comprising first opposing interior walls defining an upper channel comprising an upper impression surface adapted for engagement with a portion of the patient's upper teeth when the bite block is positioned within the patient's mouth, at least a portion of the first opposing interior walls being configured so as to at least partially converge toward the upper side of the bite block body;

a pair of lower shoulders extending from a lower side of the bite block body and comprising second opposing interior walls defining a lower channel comprising a lower impression surface adapted for engagement with a portion of the patient's lower teeth when the bite block is positioned within the patient's mouth, at least a portion of the second opposing interior walls being configured so as to at least partially converge toward the lower side of the bite block body, at least a portion of the first and second opposing interior walls comprising an impression material that is plastically deformable at or above room temperature in order to make an impression of a portion of the patient's teeth; and a tongue suppressor attached to the bite block body and oriented so as maintain the patient's tongue within a confined region of the patient's oral cavity when the bite block is positioned within the patient's mouth.

57. A customizable bite block as defined in claim 56, the tongue suppressor being adjustably attached to the bite block body in a manner so as to permit at least vertical adjustment of the tongue suppressor relative to the bite block.

* * * * *

UNITED STATES PATENT AND TRADEMARK OFFICE
CERTIFICATE OF CORRECTION

PATENT NO. : 6,652,276 B2
DATED : November 25, 2003
INVENTOR(S) : Fischer et al.

It is certified that error appears in the above-identified patent and that said Letters Patent is hereby corrected as shown below:

Column 5,
Line 30, before "FIG. 12" please remove "of"

Column 7,
Line 62, after "block 12 in" please insert -- a --

Column 18,
Line 6, after "so as" please insert -- to --

Column 21,
Line 7, after "so as" please insert -- to --

Signed and Sealed this

Twenty-first Day of September, 2004

JON W. DUDAS
*Director of the United States Patent and Trademark Office*